(12) United States Patent
Chen et al.

(10) Patent No.: US 11,116,582 B2
(45) Date of Patent: Sep. 14, 2021

(54) APPARATUS FOR DETERMINING A MOTION RELATION

(71) Applicant: KONINKLIJKE PHILIPS N.V., Eindhoven (NL)

(72) Inventors: Yinan Chen, Shanghai (CN); Junbo Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 319 days.

(21) Appl. No.: 15/751,929

(22) PCT Filed: Aug. 12, 2016

(86) PCT No.: PCT/EP2016/069309
§ 371 (c)(1),
(2) Date: Feb. 12, 2018

(87) PCT Pub. No.: WO2017/036774
PCT Pub. Date: Mar. 9, 2017

(65) Prior Publication Data
US 2018/0235708 A1    Aug. 23, 2018

(30) Foreign Application Priority Data
Aug. 28, 2015 (WO) ................ PCT/CN2015/088353
Oct. 29, 2015 (EP) .................................... 15192146

(51) Int. Cl.
*A61B 34/20* (2016.01)
*A61B 90/00* (2016.01)
(Continued)

(52) U.S. Cl.
CPC .............. *A61B 34/20* (2016.02); *A61B 5/062* (2013.01); *A61B 5/113* (2013.01); *A61B 5/7264* (2013.01);
(Continued)

(58) Field of Classification Search
None
See application file for complete search history.

(56) References Cited

U.S. PATENT DOCUMENTS 6,314,312 B1 * 11/2001 Wessels ................. A61B 90/10
600/427
6,501,981 B1 * 12/2002 Schweikard ............. A61B 6/08
378/69
(Continued)

FOREIGN PATENT DOCUMENTS

| JP | 2003275164 A | 9/2003 |
|---|---|---|
| KR | 100750279 B1 | 8/2007 |

(Continued)

OTHER PUBLICATIONS

Blackall et al: "MRI-Based Measurements of Respiratory Motion Variability and Assessment of Imaging Strategies for Radiotherapy Planning"; Phys. Med. Biol. 51 (2006), pp. 4147-4169.
(Continued)

*Primary Examiner* — Yi-Shan Yang

(57) ABSTRACT

The invention relates to an apparatus for determining a relation between a surface motion of a body (BD) and an object motion of an object (OB) within the body (BD). The apparatus comprises a first sensing unit configured to acquire a first position signal indicative of a position of a first element placed at the location on the surface of the body with the surface motion; a second sensing unit configured to acquire a second position signal indicative of a position of a second element attached to an interventional device and placed on or in the object, wherein the first position signal and the second position signal are acquired during a given duration synchronously; and a third unit for calculating the relation between the surface motion and the object motion based on the first position signal and the second position
(Continued)

signal. The invention also relates to a corresponding method for determining the motion relation.

14 Claims, 4 Drawing Sheets

(51) Int. Cl.
| | |
|---|---|
| *G16H 40/63* | (2018.01) |
| *A61B 5/06* | (2006.01) |
| *A61B 5/113* | (2006.01) |
| *A61B 5/00* | (2006.01) |
| *A61B 8/08* | (2006.01) |
| *A61B 17/00* | (2006.01) |

(52) U.S. Cl.
CPC .......... *A61B 8/0841* (2013.01); *A61B 90/37* (2016.02); *G16H 40/63* (2018.01); *A61B 2017/00699* (2013.01); *A61B 2034/2051* (2016.02); *A61B 2034/2063* (2016.02); *A61B 2034/2065* (2016.02); *A61B 2090/378* (2016.02)

(56) References Cited

U.S. PATENT DOCUMENTS

| | | | |
|---|---|---|---|
| 9,943,247 B2* | 4/2018 | Ernst | G06K 9/6256 |
| 2003/0013962 A1* | 1/2003 | Bjaerum | G01S 7/52066 |
| | | | 600/443 |
| 2006/0074292 A1 | 4/2006 | Thomson et al. | |
| 2008/0049896 A1* | 2/2008 | Kuduvalli | A61N 5/1049 |
| | | | 378/65 |
| 2009/0180666 A1 | 7/2009 | Sheng et al. | |
| 2009/0198298 A1* | 8/2009 | Kaiser | A61N 1/3627 |
| | | | 607/17 |
| 2010/0113919 A1* | 5/2010 | Maschke | A61B 17/221 |
| | | | 600/424 |
| 2012/0209117 A1* | 8/2012 | Mozes | G06F 3/043 |
| | | | 600/439 |
| 2012/0226152 A1* | 9/2012 | Porikli | A61N 5/1068 |
| | | | 600/427 |
| 2013/0018232 A1* | 1/2013 | D'Souza | A61N 5/1049 |
| | | | 600/300 |
| 2013/0165770 A1 | 6/2013 | Li et al. | |
| 2015/0051480 A1 | 2/2015 | Hwang et al. | |
| 2015/0265368 A1* | 9/2015 | Chopra | A61B 5/7425 |
| | | | 600/424 |

FOREIGN PATENT DOCUMENTS

| | | |
|---|---|---|
| WO | 9840026 A1 | 9/1998 |
| WO | 2005070318 A1 | 8/2005 |
| WO | 2006000789 A1 | 1/2006 |
| WO | 2012066494 A2 | 5/2012 |
| WO | 2012142031 A1 | 10/2012 |
| WO | 2012168869 A1 | 12/2012 |
| WO | 2013190451 A1 | 12/2013 |

OTHER PUBLICATIONS

De Silva et al: "2D-3D Rigid Registration to Compensate for Prostate Motion During 3D Trus-Guided Biopsy"; Med.Phys.40(2), Feb. 2012, pp. 022904-1-022904-13.

Gierga et al: "The Correlation Between Internal and External Markers for Abdominal Tumors:Implications for Respiratory Gating"; Int. J. Radiation Oncology Biol. Phys., vol. 61, No. 5, pp. 1551-1558, 2005.

Rohlfing et al: "Modeling Liver Motion and Deformation During the Respiratory Cycle Using Intensity-Based Nongrid Registration of Gated MR Images"; Med. Phys. 31(3), Mar. 2004, pp. 427-432.

Wu et al: "Fast and Robust Extraction of Surrogate Respiratory Signal From Intra-Operative Liver Ultrasound Images"; Int. J. Cars (2013) 8:1027-1035.

Yang et al: "Subject-Specific Real-Time Respiratory Liver Motion Compensation Method for Ultrasound-MRI/CT Fusion Imaging"; Intj. Cars (2015) vol. 10, pp. 517-529.

Mung et al: "Ultrasound-Enhanced Catheter Visualization and Tracking:Prototype Description and In Vitro Results".

* cited by examiner

APPARATUS FOR DETERMINING A MOTION RELATION

CROSS-REFERENCE TO PRIOR APPLICATIONS

This application is the U.S. National Phase application under 35 U.S.C. § 371 of International Application Serial No. PCT/EP2016/069309, filed on Aug. 12, 2016, which claims the benefit of PCT/CN2015/088353, filed on Aug. 28, 2015 and EP15192146.7, filed on Oct. 29, 2015. This application is hereby incorporated by reference herein.

FIELD OF THE INVENTION

The invention relates to a method and apparatus for determining a relation between a motion of a location on a surface of a body and a motion of an object within the body.

BACKGROUND OF THE INVENTION

Image-guided intervention (IGI) therapy is widely used in cancer treatment or therapy. The purpose of IGI therapy is to kill the pathology occurring in an object in a patient body, for example, tumor cells. The IGI therapy is navigated by images of the object. During IGI therapy, thermal ablation is usually used repeatedly and in conjunction with other treatment options. This is done by delivering some energy to the object in the patient body, for example, in the form of radio frequency or microwave ablation.

However, during the whole IGI therapy process, patient body motion, for example, motion caused by respiratory, may produce inaccuracy on the position where to put the interventional needle and where thermal ablation is applied. Indeed, the position of the object in the patient body may change with the respiratory motion. The position change of the object in the patient body is not the same as the position change of the surface of the patient body. Measuring the corresponding surface motion is not accurate enough to reflect the object motion in the patient body.

The publication Int J CARS (2013) 8:1027-1035 discloses a method to build a motion model based on position information of a human body surface and position information of an object in the human body. The position information of the object is obtained by processing acquired ultrasound images of the object. When using ultrasound imaging, ultrasound echo is not accurate enough to detect the object which is in a deep position in the human body. Ultrasound imaging also has the problem of low resolution. Therefore, by using this method, the accuracy of building a relation between a motion of a location on a surface of the body and a motion of an object within the body is not good. Similar to publication Int J CARS, WO 2012/066494 A2 discloses an apparatus that generates a motion model based on external marker characteristics and internal motion. The internal motion is derived from a sequence of images of the lesion or target over time t. WO 2006/000789 A1 discloses to correlate the internal tissue movement with the external body surface movement by tracking external surface movement at a plurality of surface points, simultaneously imaging internal tissue movement and correlating the external and internal movement using partial lease squares regression.

OBJECT AND SUMMARY OF THE INVENTION

It is an object of the invention to provide a method and apparatus which determines a relation between a surface motion of a body and an object motion of an object within the body with high accuracy.

According to a first aspect of the present invention the object is achieved by an apparatus for determining a relation between a surface motion of a location on a surface of a body and an object motion of an object within the body, the apparatus comprising:

a first sensing unit configured to acquire a first position signal indicative of a position of a first element placed at the location on the surface of the body with the surface motion;

a second sensing unit configured to acquire a second position signal indicative of a position of a second element attached to an interventional device and placed on or in the object, wherein the first position signal and the second position signal are acquired during a given duration synchronously; and a third unit for calculating the relation between the surface motion and the object motion based on the first position signal and the second position signal.

With this apparatus, the object motion is measured directly based on the position signal of the second element attached to the interventional device, e.g., by simply placing the second element attached to the interventional device on or in the object within the body More specifically, the second element is attached to the tip of the interventional device. When the tip of the interventional device punctures to the object surface, a modeling stage that builds a surrogate model defining a relation between the body surface motion and the object motion is triggered. The interventional device stays in the same place inside the body in the modeling stage so that the second element moves together with the object and the movement sensed by the second element is solely from the internal object motion, e.g., due to respiration effect. Meanwhile, the position of the first position signal sensed by the first element placed on the body surface is captured synchronously with each respiration depth. Such direct object motion measurement is proposed based on the discovery of the inventors that although speckle tracking technology can be used for tracking the object motion from the ultrasound images, speckle noises and poor image quality of the ultrasound images limit the accuracy of the object motion tracking and such inaccuracy is a main cause of failure of respiration motion compensation. Moreover, the present invention performs the direct object motion measurement by leveraging the second element normally attached to the interventional device for interventional device tracking purposes. More specifically, instead of tracking the location of the interventional device, the second element attached to the interventional device is switched to measure the object motion directly for building the surrogate model. Upon completion of the surrogate model building, the second element attached to the interventional device is switched back to the normal interventional device tracking. By leveraging the second element normally attached to the interventional device for additional object motion measurement, no extra hardware and/or software is introduced and no extra surgery is performed to place the second element on or in the object. Consequently, a more cost-effective, user-friendly, and robust apparatus for determining the relation between the object surface motion and internal object motion is achieved.

The first position information and the second position information may be accurately acquired by choosing a proper sensing unit. It improves the accuracy of detecting position changes of the object within the body caused by respiratory motion.

Subsequently, based on the acquired first position information and second position information, building up the relation between the body surface motion and the object motion has high accuracy.

An embodiment of the present invention is an apparatus wherein the first sensing unit comprises a first signal unit adapted to generate first given signals towards a region of the surface of the body, wherein the first element comprises a first receiver adapted to be placed on the surface and in the region of the surface, and wherein the first sensing unit is adapted to derive the first position signal on the basis of the first given signals sensed by the first receiver.

Putting the first receiver on the surface of the body is easy to operate and allows detecting the signal indicative of the position of the surface of the body in high accuracy.

An embodiment of the present invention is an apparatus adapted to derive a first position information on the basis of the first position signal and the first given signals generated by the first signal unit.

An embodiment of the present invention is an apparatus wherein the second sensing unit comprises a second signal unit adapted to generate second given signals towards the object, wherein the second element comprises a second receiver adapted to be placed on or in the object, and wherein the second sensing unit is adapted to derive the second position signals on the basis of the second given signals sensed by the second receiver.

Putting the second receiver on or in the object within the body allows detecting the signal indicative of the position of the object in high accuracy.

An embodiment of the present invention is an apparatus adapted to derive a second position information on the basis of the second position signal and the second given signals generated by the second signal unit.

Deriving the second position information allows obtaining direct position information of the object in the body.

An embodiment of the present invention is an apparatus wherein the first signal unit is an electromagnetic field generator, wherein the first receiver is a coil, and wherein the apparatus is arranged to measure a voltage generated in the first receiver.

Putting the coil on the patient body is easy to operate for a user and safe for the patient. Generating a magnetic field is easy to operate for a user and is safe for the patient when being applied during the whole therapy procedure.

An embodiment of the present invention is an apparatus wherein the second signal unit comprises an ultrasound probe, wherein the second receiver is an ultrasound acoustic sensor and wherein the apparatus is adapted to identify (i) a beam detected by the second receiver and (ii) a corresponding time duration for detecting the beam.

Putting the ultrasound acoustic sensor in the object within the patient body is safe for the patient. Generating ultrasound signals is easy to operate for a user and is safe for the patient when being applied for the whole therapy procedure. In addition, by using acoustic sensor, the 2D/3D position of the acoustic sensor is obtained by processing the ultrasound imaging beams received by it as the ultrasound imaging beams sweep the field of view during conventional imaging pulse-echo acquisition, in which the angular position information is derived by processing the angular direction of the ultrasound beams that hit the acoustic sensor with highest amplitude, and the range information is derived from the time-of-flight from emission of these beams to reception by the acoustic sensor attached to the interventional device. Since both the acoustic tracking and pulse-echo ultrasound imaging use the same ultrasound beams, bias-free co-registration of the position of the acoustic sensor and the ultrasound image is achieved by design, without the need of equipping external tracking system, e.g., external electromagnetic field generator for EM-based tracking of EM sensors. In addition to the competitive tracking accuracy, acoustic based tracking is more cost-effective and anti-interference, e.g., anti-electromagnetic interference. An embodiment of the present invention is an apparatus adapted to derive first position information of the first receiver based on the measured voltage and on electromagnetic positioning calculation.

Using the given mapping allows deriving the first position information accurately based on the connection between the currents generated in the first receiver and corresponding position information in the region of the first given signals, i.e., a magnetic field generated by the electromagnetic unit.

An embodiment of the present invention is an apparatus adapted to:

calculate a distance from the second receiver to the second signal unit based on the corresponding time duration and a given velocity, and derive second position information of the second receiver based on the distance and the information of the beam.

Using the above apparatus allows deriving the position information of the second sensor accurately based on the given velocity of ultrasound signal and signals sensed by the ultrasound acoustic sensor.

An embodiment of the present invention is an apparatus wherein the third unit for calculating is adapted to calculate the relation between the motion of the location on the surface of the body and the motion of the object on the basis of machine learning algorithms comprising non-linear fitting, neural network, or logic regression.

Applying machine learning algorithms provides an automatic approach to calculate the motion relation.

In another embodiment of the apparatus according to the present invention, the second element attached to the interventional device is further configured to track a location of the interventional device. Furthermore, the apparatus is configured to switch the operation of the second element from object motion measurement to interventional device tracking upon completion of determining the relation between the surface motion and the object motion. Attaching the second receiver on the interventional device allows placing the second receiver on or in the object within the patient body conveniently when inserting the interventional device in the object, which improves the patient comfort since no extra surgery is performed to place the second receiver on or in the object. Also, by switching the second element normally attached to the interventional device from the normal interventional device tracking to additional object motion measurement, no extra hardware and/or software is introduced to provide a cost-effective solution.

In another embodiment of the apparatus according to the present invention, the given duration is chosen to be at least one respiratory cycle of the body of a living being.

The information of at least one respiratory cycle allows obtaining complete motion information within a respiratory cycle. Therefore, a complete motion relation within a respiratory cycle may be derived.

In another embodiment of the apparatus according to the present invention, the apparatus is adapted to be connected to a display for displaying at least a given image of the object and the position information of the second element based on the second position signal.

The display allows visualizing at least the image of the object and the position information of the second element on a screen.

According to a second aspect of the present invention, a method is provided for determining a relation between a surface motion of a location on a surface of a body and an object motion of an object within the body, the method comprising:

a first step of acquiring a first position signal indicative of a position of a first element placed at the location on the surface of the body with the surface motion;

a second step of acquiring a second position signal indicative of a position of a second element attached to an interventional device and placed on or in the object, wherein the first position signal and the second position signal are acquired during a given duration synchronously;

a third step of calculating the relation between the surface motion and the object motion based on the first position signal and the second position signal.

Detailed explanations and other aspects of the invention will be given below.

BRIEF DESCRIPTION OF THE DRAWINGS

Particular aspects of the invention will now be explained by way of examples with reference to the embodiments described hereinafter and considered in connection with the accompanying drawings, in which identical parts or substeps are designated in the same manner.

DETAILED DESCRIPTION OF THE INVENTION

Figure 1:
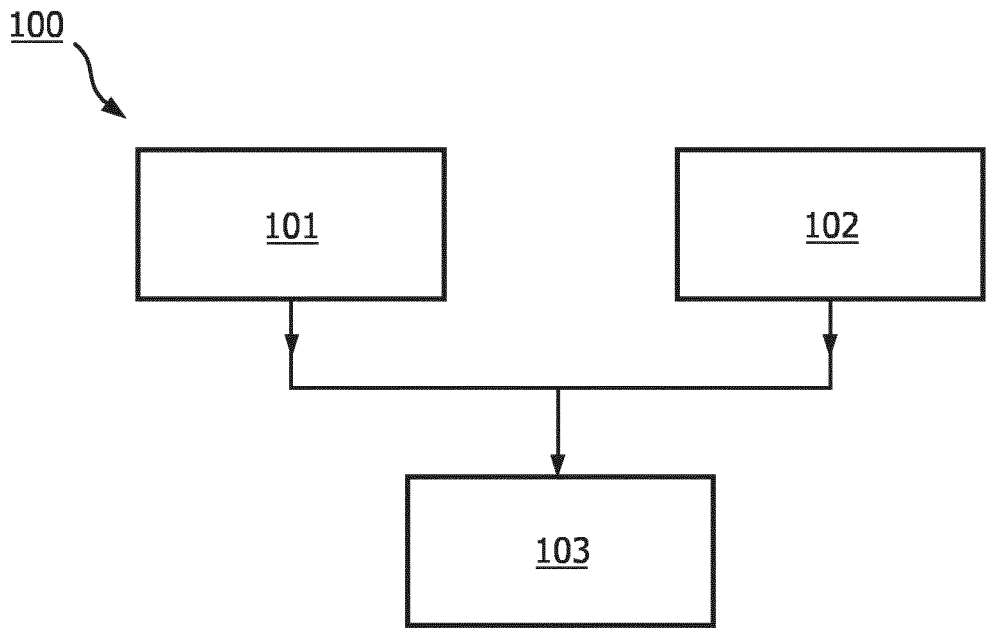
FIG. 1 depicts a flowchart for determining a motion relation according to the present invention.

IGI therapy is a treatment widely used in cancer treatment or more generally in medical therapy, for example. IGI therapy used in cancer treatment aims to kill tumor cells in an organ of a patient body by delivering energy to the position of the tumor navigated by acquired images of the organ. In the following, the organ in the patient body which receives the energy is described as "object". The object of the patient body may have a movement, for example, during a therapy for a tumor in the object of a patient body, the object may have a certain movement caused by respiration of the patient.

Before the start of the therapy, an object of a patient body is scanned with a medical imaging system to acquire images, for example, CT and MRI, etc. For example, the scan is done a few hours or minutes before the therapy. These images are acquired while the patient is asked to hold his/her breath to avoid body movement caused by the respiration of the patient.

During the therapy, the patient lies horizontally, for example, on a bed. During the therapy, images of the object are required to be visualized in order to provide adequate and accurate guidance for a surgeon while surgical instruments are manipulated by the surgeon. For example, an interventional device is operated by the surgeon to be inserted into the object and deliver energy to the targeted tumor position.

During the therapy, the images being visualized for guiding the intervention are a combination of acquired CT/MRI images and the position information of the interventional device. Based on the visualized images, the surgeon knows where the interventional device is and where to proceed.

However, during the therapy, the object position changes due to body movement caused by respiration of the patient. Because the interventional device is inserted in the object, the movement of the interventional device reflects the movement of the object.

CT/MRI images contain the information of the object. These CT/MRI images are acquired before the therapy under the condition of absence of respiratory movement of the patient. The interventional device position information is acquired during the therapy which varies with respiratory movement of the patient body. Therefore, at a certain given moment within a respiratory cycle of the patient body, the acquired CT/MRI images need to be visualized together with the position information of the interventional device. Thus motion compensation for acquired CT/MRI images is needed.

The surface position of the patient body also changes due to body movement caused by respiration of the patient. The position change of the object in the patient body is not the same as the position change of the surface of the patient body. Measuring the corresponding surface motion is not accurate enough to reflect the object motion in the patient body. The inventors recognized that the relation between a motion of the surface of the patient body and of an organ of the patient body is stable over time. Determining the relation between a motion of a location on a surface of the body and a motion of an object within the body helps to reflect accurate motion of the object for motion compensation. Based on the relation, the motion of the object within the body is derived from the motion of the location on a surface of the body, which may be used in usual motion compensation.

Based on a position of the interventional device and the determined motion relation, an accurate motion compensation is applied for CT/MRI images acquired before the therapy. The motion information is sent to a processor used for the therapy, for example, an ultrasound processor. The processor uses this motion information for compensating the motion of the object in the patient body, resulting in identifying the CT/MRI images to be visualized at this certain moment, even if the object has a certain movement.

According to the invention, a relation between a motion of a location on a surface of a body BD and a motion of an object OB within the body BD is determined, as will be detailed hereinafter.

The object OB may comprise various types of objects, of which the position information needs to be determined. For example, in the field of IGI therapy, the object OB corresponds to a tissue or organ in the patient body.

FIG. 1 depicts a flowchart for determining a motion relation according to the invention.

The method comprises a first step of acquiring 101 by means of a first sensing unit SEU1 a first position signal indicative of a position of a first element placed at the location on the surface of the body BD.

The first sensing unit SEU1 may generate signals and/or sense signal changes in the region of the generated signals.

The first element implemented may be chosen from a plurality of technologies, for example, electromagnetic field calculation, optical technology, X-ray technology, camera technology and radar technology etc. The embodiment of the first element is not limited to these mentioned technologies.

The method further comprises a second step of acquiring 102 by means of a second sensing unit SEU2, a second position signal indicative of a position of a second element placed on or in the object OB, the first position signal and the second position signal being acquired during a given duration synchronously.

The second sensing unit SEU2 may generate signals and/or sense signal changes in the region of the generated signals.

The second element implemented may be chosen from a plurality of technologies, for example, electromagnetic calculation, ultrasound technology, and fiber optic gyroscope technology etc. The embodiment of the second element is not limited to these mentioned technologies.

The method further comprises a third step of calculating 103 the relation between the motion of the location on the surface of the body and the motion of the object OB based on the first position signal and the second position signal.

The relation reflects a trend between the position change of the second location on or in the object OB and the position change of the location on the surface of the body BD. For a given first position on the surface of the body BD, the corresponding second location on or in the object OB is derived based on the relation.

Advantageously, the motion is respiratory motion of the body BD of a living being.

The motion of the body BD may be caused by various motions. Respiratory motion of the body BD is a common motion which is a periodic motion.

Figure 2:
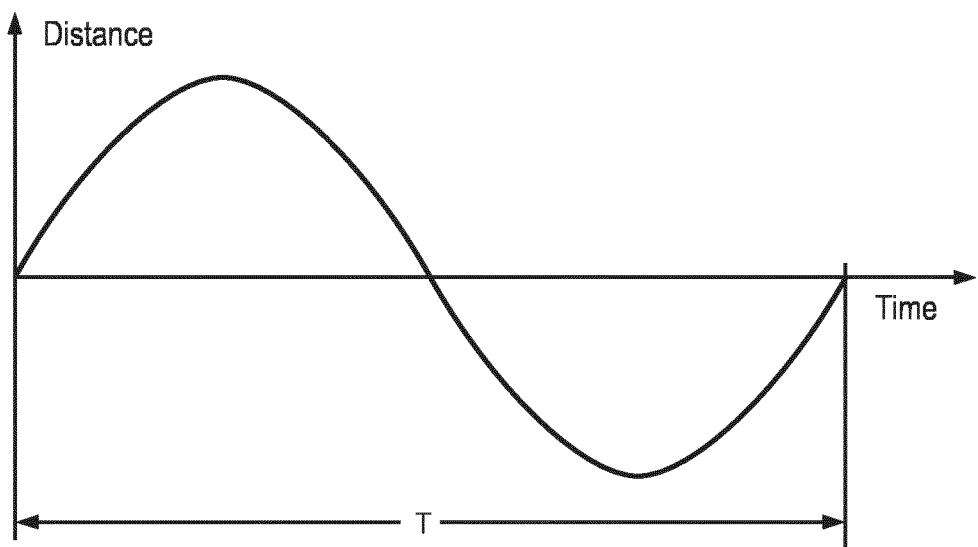
FIG. 2 illustrates an example of a displacement model of a body according to the present invention.

FIG. 2 illustrates an example of a displacement model of a body according to the present invention.

The horizontal axis corresponds to the time and the vertical axis corresponds to the displacement of the body BD. The displacement model reflects the position of the body BD varying with respect to time. The displacement model is a typically periodical curve because the motion is caused by respiratory motion. One periodical time cycle is T.

Advantageously, the given duration is chosen to be at least one respiratory cycle of the body BD of a living being.
As an example, experiments show that the given duration chosen in the range [T; 10T] is realistic.

Advantageously, the first sensing unit SEU1 comprises a first signal unit SU1 generating first given signals SG1 towards a region of the surface of the body BD, the first element comprises a first receiver R1 placed on the surface and in the region of the surface, the first position signals being derived on the basis of the first given signals SG1 sensed by the first receiver R1.

Figure 3A:
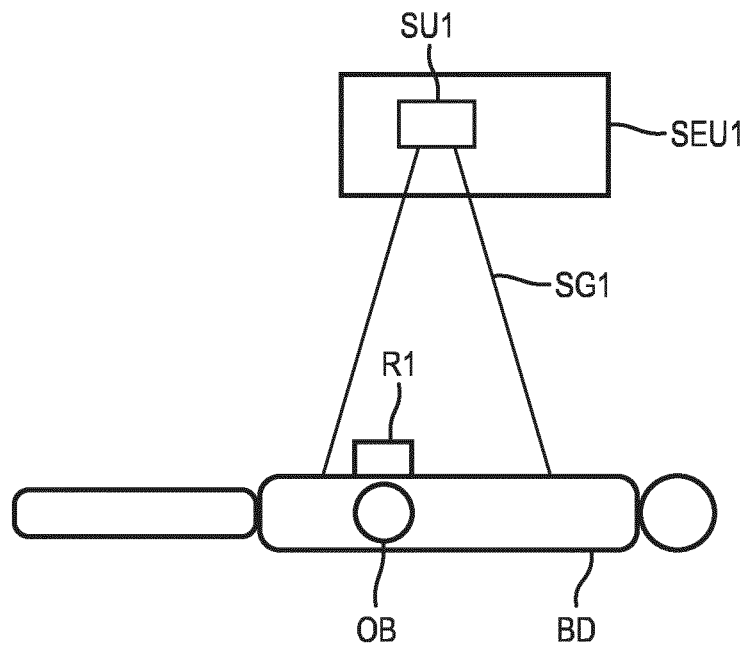
FIG. 3A, 3B illustrate embodiments according to the present invention.

FIG. 3A illustrates an embodiment of sensing unit SEU1 for use in step 101 of the method according to the present invention.

In this embodiment the first element is placed on a location of the surface of the body BD. For example, the object OB is the liver in the body BD, the first receiver R1 is chosen to be placed on an adjacent location of the surface above the liver when a patient lies on a bed. The first signal unit SU1 generates the first given signals SG1 towards the region of the adjacent location of the surface above the liver, for example, around the midclavicular line.

For example, the first signal unit SU1 generates light beams. The first receiver R1 effects, for example, reflections of the light beams. These reflections can be determined by optical sensors, which derive, using usual position detection technology, position information indicating the accurate position of the first element.

Another example is that the first signal unit SU1 generates rontgen radiation beams. The position of the first element is detected by usual rontgen technologies for detecting position of the first element.

There are other alternative technologies. For example, electromagnetic technology is based on sensing the magnetic field and calculations based on electromagnetic field distribution.

The technologies enabling to determine the position of the first element are not limited to the above-mentioned technologies.

In step 101 a first position information is derived on the basis of the first position signal and the first given signals SG1 generated by the first signal unit SU1.

The first position information indicates the accurate position of the first element.

Figure 4:
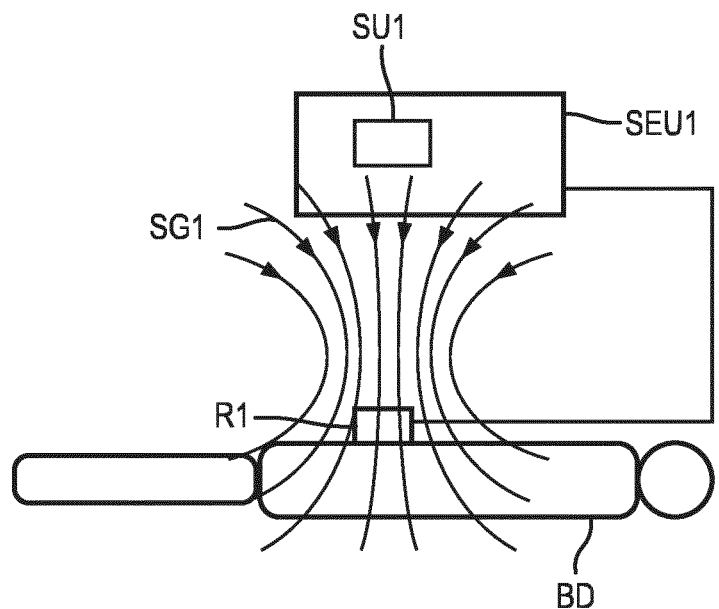
FIG. 4 illustrates an embodiment of a first sensing unit according to this invention.

FIG. 4 illustrates an embodiment of the first sensing unit SEU1 using a coil for determining the position of the first element in step 101 of the method according to the invention.

The electromagnetic field generator is a continuous, three-dimensional, position-locating device/unit based on electromagnetic technology. The electromagnetic field generator generates a magnetic field towards the location of the surface of the body BD.

The coil is placed on the surface of the body BD to indicate a location on the surface of the body BD. The coil is also in the generated magnetic field. The magnetic field created by the electromagnetic field generator induces a voltage in the coil, which is measured by the connected first sensing unit SEU1.

In this embodiment, one coil is used for the purpose of illustration. The alternative embodiments are not limited to using one coil.

Advantageously, the first position information of the first receiver R1 is based on the measured voltage and the electromagnetic positioning calculation.

The first sensing unit SEU1 continuously calculates the position and orientation of the coil. The first position information of the coil is calculated based on the measured voltage and the electromagnetic positioning calculation, which depends on the distribution of the magnetic field generated by the first signal unit SU1.

Advantageously, the second sensing unit SEU2 comprises a second signal unit SU2 generating second given signals SG2 towards the object OB, the second element comprises a second receiver R2 placed within the body BD on or in the object OB, the second position signals being derived on the basis of the second given signals SG2 sensed by the second receiver R2.

Figure 3B:
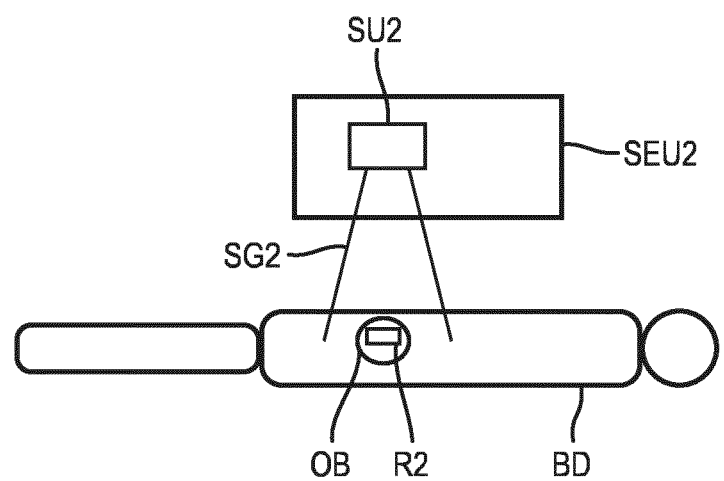

FIG. 3B illustrates an embodiment of the second sensing unit SEU2 for use in step 102 of the method according to the invention.

The second element is placed on or in the object OB within the body BD. For example, the object OB is the liver in a body BD, the second element is placed in the liver.

The second signal unit SU2 generates the second given signals SG2 towards the region of the object OB within the body BD.

The second receiver R2 is placed in the liver and arranged to receive the second given signals SG2.

For example, the second signal unit SU2 generates ultrasound acoustic beams. The second receiver R2 effects, for example, reception of the ultrasound acoustic beams. The position of the second element is derived from the information received by ultrasound acoustic sensors and usual ultrasound acoustic sensing technologies.

Another example is that the second signal unit SU2 generates a magnetic field. The second receiver R2 effects, for example, the introduction of a voltage in the magnetic field. The induced voltage is determined by a coil, which derives the accurate position of the second element through usual electromagnetic calculation.

Other alternative technology, for example, fiber optic gyroscope, determines the location of the second element based on sensing and analyzing the beams within fiber optic cables.

The technologies enabling to determine the position of the second element are not limited to the above-mentioned technologies.

Advantageously, the second step of acquiring 102 further comprises a step of deriving a second position information on the basis of the second position signal and the second given signals SG2 generated by the second signal unit SU2.

The second position information indicates the accurate position of the second element.

Figure 5:
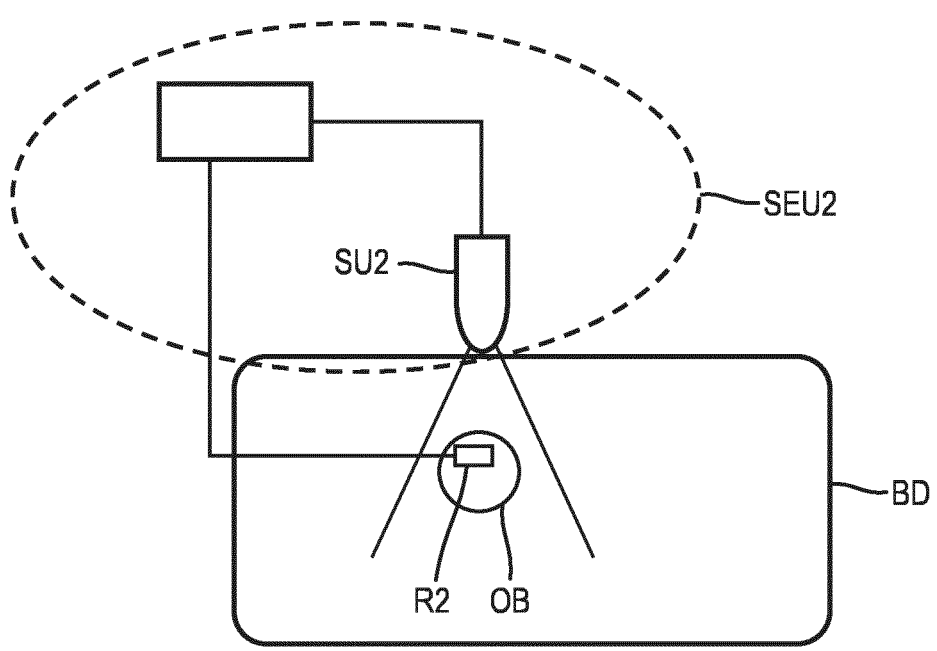
FIG. 5 illustrates an embodiment of a second sensing unit according to the present invention.

FIG. 5 illustrates an embodiment of the second sensing unit SEU2 using an ultrasound acoustic sensor for determining the position of the second element in step 102 of the method according to the invention.

In this embodiment, the second receiver R2 is an ultrasound acoustic sensor and the second signal unit SU2 comprises an ultrasound probe. As illustrated in FIG. 5, the ultrasound probe is placed on the surface above the object OB, for example, above the liver. The ultrasound acoustic sensor is placed in the object OB within the body BD.

The operation of the ultrasound acoustic sensor is based on measuring the properties of ultrasound acoustic waves with a frequency above the human audible range. The ultrasound probe generates ultrasound acoustic waves towards the object OB within the body BD. The ultrasound acoustic sensor is in the region of the ultrasound acoustic waves and receives the ultrasound acoustic waves.

Figure 6:
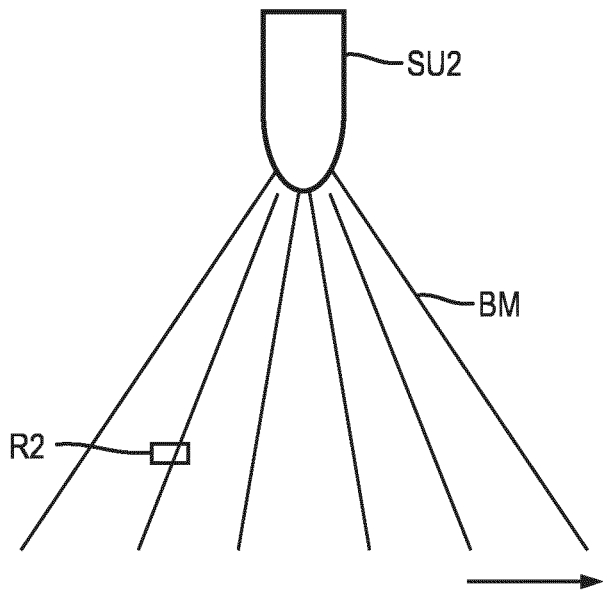
FIG. 6 illustrates an example of receiving ultrasound acoustic beams according to the present invention.

FIG. 6 illustrates an example of receiving ultrasound acoustic beams BM according to the present invention.

The ultrasound acoustic waves are generated in the form of ultrasound acoustic beams BM. The ultrasound acoustic beams BM sweep the field of view during data acquisition. As illustrated in FIG. 6, the ultrasound acoustic beams BM are swept in the direction of the arrow. One beam is illustrated as one line in FIG. 6.

The ultrasound acoustic sensor has the capability of receiving one of the beams. When the ultrasound acoustic sensor receives one beam, the second signal unit SU2 acquires the information as to which beam is received by the ultrasound acoustic sensor. Meanwhile, the time duration for receiving the beam is also acquired, which is from emission of the beam to reception by the ultrasound acoustic sensor.

Advantageously, the second step of deriving comprises the sub steps of:

calculating a distance from the second receiver R2 to the second signal unit SU2 based on the corresponding time duration and a given velocity.

deriving the second position information of the second receiver R2 based on the distance and the information of the beam.

Based on the signals acquired by the second sensing unit SEU2, the distance from the second receiver R2 to the second signal unit SU2 is calculated, for example, the distance between the ultrasound acoustic sensor and the ultrasound probe. The distance is calculated by multiplying the above mentioned acquired time duration and a given velocity. The given velocity is 1540 m/s for ultrasound acoustic waves.

The second position information is derived based on the calculated distance and the information of the beam acquired as mentioned above. For example, the position information of the ultrasound acoustic sensor is derived from the position of the ultrasound probe along the identified beam.

Advantageously, the second receiver R2 is adapted to be attached to an interventional device.

The second receiver R2 is placed on or in the object OB within the body BD. In order to do that for IGI therapy, for example, the ultrasound acoustic sensor is attached to the interventional device, such as metal needle or rubber catheter. The interventional device is inserted into the object OB within the body BD during the therapy. The second receiver R2 attached to the invention device accordingly to the invention is consequently put in the object OB.

Advantageously, the step of calculating 103 is based on machine learning algorithms comprising non-linear fitting, neural network, or logic regression.

Applying machine learning algorithms is to build up a model by training available datasets, in order to make predictions or decisions based on a given dataset.

The machine learning algorithms are not limited to non-linear fitting, neural network and logic regression.

Figure 7:
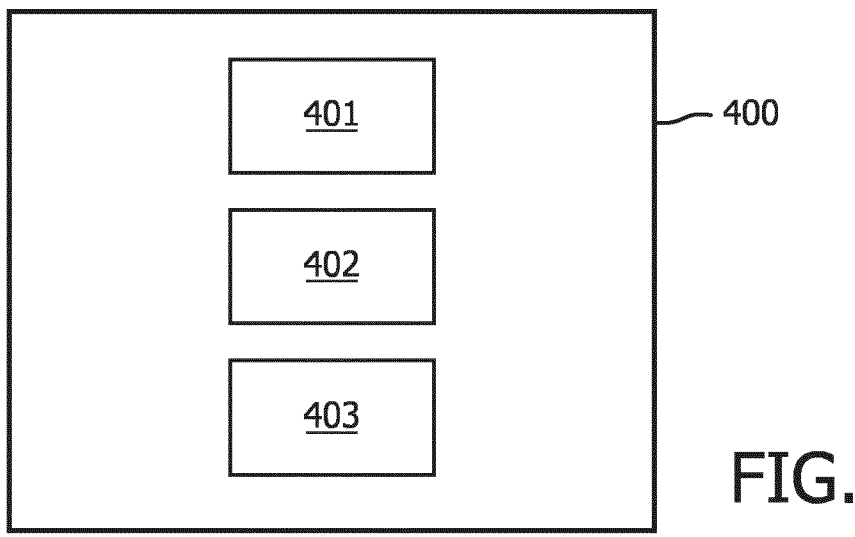
FIG. 7 depicts a schematic diagram of an apparatus according to the present invention.

FIG. 7 depicts a schematic diagram of an apparatus 400 according to the present invention to determine a motion relation. The apparatus 400 comprises:

a first unit for acquiring 401 by means of a first sensing unit SEU1 a first position signal indicative of a position of a first element placed at the location on the surface of the body BD;

a second unit for acquiring 402 by means of second sensing unit SEU2 a second position signal indicative of a position of a second element placed on or in the object OB, wherein the first position signal and the second position signal are acquired during a given duration synchronously;

a third unit for calculating 403 the relation between the motion of the location on the surface of the body and the motion of the object OB based on the first position signal and the second position signal.

The various units of the apparatus according to the invention are adapted to carry out the various steps described previously.

Figure 8:
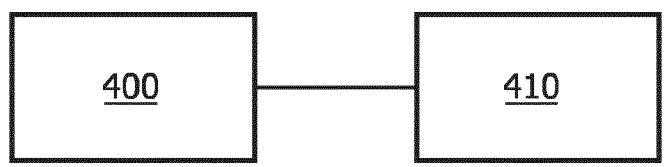
FIG. 8 depicts a schematic diagram of an apparatus according to an embodiment of the present invention.

FIG. 8 depicts a schematic diagram of an apparatus according to an embodiment of the present invention.

Advantageously, the apparatus 400 is adapted to be connected to a display 410 for displaying at least a given image of the object OB and the position information of the second element based on the second position signal.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the spirit and scope of the technique approaches of the present invention, which will also fall into the protective scope of the claims of the present invention. In the claims, the word "comprising" does not exclude other elements or steps, and the indefinite article "a" or "an" does not exclude a plurality. Any reference signs in the claims should not be construed as limiting the scope.

The invention claimed is:

1. An apparatus for determining a relation between a surface motion at a location on a surface of a body (BD) and an object motion of an object (OB) within the body (BD), the apparatus comprising:
- a first element adapted to be placed at the location on the surface of the body (BD), wherein the location on the surface of the body is subject to cyclical surface motion caused by respiration of the body;
- a first sensing unit (SEU1) configured to acquire a first position signal indicative of a position of the first element placed at the location on the surface of the body (BD);
- a second element attached to an interventional device and adapted to be placed on or in the object (OB) to facilitate direct object motion measurement, wherein the object (OB) is subject to cyclical object motion caused by the respiration of the body, further wherein (i) a position change of the second element due to movement of the object (OB) within the body (BD) caused by the respiration of the body is different from (ii) a position change of the first element at the location on the surface of the body due to movement at the location on the surface of the body caused by the respiration of the body;
- a second sensing unit (SEU2) configured to acquire a second position signal indicative of a position of the second element attached to the interventional device and adapted to be placed on or in the object (OB); and
- a third unit, operable during a modeling stage, for building a surrogate model defining the relation between the surface motion and the object motion, wherein building the surrogate model comprises calculating the relation between the surface motion and the object motion based on the first position signal and the second position signal having been acquired, via the respective first sensing unit and the second sensing unit, during a given duration synchronously,
- wherein the second element is further configured to facilitate location tracking of the interventional device during an interventional device tracking stage, and
- wherein the third unit is further configured to switch an operation of the second element from the direct object motion measurement to the location tracking for the interventional device upon completion of the modeling stage.

2. The apparatus as claimed in claim 1,
- wherein the first sensing unit (SEU1) comprises a first signal unit (SU1) adapted to generate first given signals (SG1) towards a region of the surface of the body that includes the location,
- wherein the first element comprises a first receiver (R1) adapted to be placed on the location on the surface of the body, and
- wherein the first sensing unit (SEU1) is further configured to acquire the first position signal by deriving the first position signal based on a characteristic of the first given signals (SG1) sensed by the first receiver (R1).

3. The apparatus as claimed in claim 2, wherein the first sensing unit (SEU1) is further configured to derive first position information based on the first position signal and the first given signals (SG1) generated by the first signal unit (SU1).

4. The apparatus as claimed in claim 2,
- wherein the first signal unit (SU1) is an electromagnetic field generator configured to generate an electromagnetic field,
- wherein the first receiver (R1) is a coil, and
- wherein the first sensing unit (SEU1) is further configured to measure a voltage generated in the first receiver (R1) in response to the coil sensing the electromagnetic field.

5. The apparatus as claimed in claim 4, wherein the first sensing unit (SEU1) is further configured to derive first position information of the first receiver (R1) based on the measured voltage and on electromagnetic positioning calculation.

6. The apparatus as claimed in claim 1,
- wherein the second sensing unit (SEU2) comprises a second signal unit (SU2) adapted to generate second given signals (SG2) towards the object (OB),
- wherein the second element comprises a second receiver (R2) adapted to be placed on or in the object (OB), and
- wherein the second sensing unit is further configured to acquire the second position signal by deriving the second position signal based on a characteristic of the second given signals (SG2) sensed by the second receiver (R2).

7. The apparatus as claimed in claim 6, wherein the third unit is further adapted to derive second position information based on the second position signal and the second given signals (SG2) generated by the second signal unit (SU2).

8. The apparatus as claimed in claim 6,
- wherein the second signal unit (SU2) comprises an ultrasound probe configured to generate ultrasound beams,
- wherein the second receiver (R2) is an ultrasound acoustic sensor, and
- wherein the second sensing unit (SEU2) is further configured to identify (i) an ultrasound beam detected by the second receiver (R2) and (ii) a corresponding time duration for detecting the ultrasound beam.

9. The apparatus as claimed in claim 8, wherein the second sensing unit (SEU2) is further configured to:
- calculate a distance from the second receiver (R2) to the second signal unit (SU2) based on a corresponding time duration and a given velocity of the ultrasound beam, and
- derive second position information of the second receiver (R2) based on the distance and information of the ultrasound beam.

10. The apparatus as claimed in claim 7, further comprising a display for displaying at least a given image of the object OB and the second position information of the second element.

11. The apparatus as claimed in claim 1, wherein the third unit for calculating is adapted to calculate the relation between the surface motion and the object motion further based on machine learning algorithms that comprises one or more of non-linear fitting, neural network, or logic regression.

12. The apparatus as claimed in claim 1, wherein the surface motion and the object motion are each a function of respiratory motion of the body (BD), and wherein the object motion which corresponds to position changes of the second element due to movement of the object (OB) within the body (BD) caused solely by the respiration is different from the surface motion which corresponds to position changes of the first element at the location on the surface of the body due to movement at the location on the surface of the body caused solely by the respiration.

13. The apparatus as claimed in claim 1, wherein the given duration is at least one respiratory cycle of the body (BD).

14. A method for determining a relation between a surface motion at a location on a surface of a body (BD) and an object motion of an object (OB) within the body (BD), the method comprising:
  acquiring, via a first sensing unit, a first position signal indicative of a position of a first element placed at the location on the surface of the body (BD) wherein the location at the surface of the body is subject to cyclical surface motion caused by respiration of the body;
  acquiring, via a second sensing unit, a second position signal indicative of a position of a second element attached to an interventional device and placed on or in the object (OB) to facilitate direct objection motion measurement, wherein the object (OB) is subject to cyclical object motion caused by the respiration of the body, further wherein (i) a position change of the second element due to movement of the object (OB) within the body (BD) caused by the respiration of the body is different from (ii) a position change of the first element at the location on the surface of the body due to movement at the location on the surface of the body caused by the respiration of the body;
  budding, via a third unit operable during a modeling stage, a surrogate model defining the relation between the surface motion and the object motion, wherein budding the surrogate model comprises calculating the relation between the surface motion and the object motion based on the first position signal and the second position signal having been acquired, via the respective first sensing unit and the second sensing unit, during a given duration synchronously;
  wherein the second element is further configured to facilitate location tracking of the interventional device during an interventional device tracking stage, and
  wherein the third unit is further configured to switch an operation of the second element from the direct object motion measurement to the location tracking for the interventional device upon completion of the modeling stage.

* * * * *